United States Patent [19]

Gopon

[11] Patent Number: 4,898,359
[45] Date of Patent: Feb. 6, 1990

[54] BASE FOR HOLDING A PLASTER OF PARIS MODEL OF A SET OF TEETH

[75] Inventor: Günter Gopon, Karlsruhe, Fed. Rep. of Germany

[73] Assignee: Karsten Baumann, Muhlacker, Fed. Rep. of Germany

[21] Appl. No.: 193,009

[22] Filed: May 12, 1988

[30] Foreign Application Priority Data

May 14, 1987 [DE] Fed. Rep. of Germany ....... 3716143

[51] Int. Cl.$^4$ ............................................ A61C 11/00
[52] U.S. Cl. ........................................ 249/54; 249/98; 249/176; 264/17; 433/74; 433/213
[58] Field of Search .................... 433/60, 74, 75, 213, 433/214; 249/54, 83, 98, 176, 177; 264/16–19

[56] References Cited

U.S. PATENT DOCUMENTS

| | | | |
|---|---|---|---|
| 3,581,398 | 6/1971 | Thomas | 433/74 |
| 4,022,419 | 5/1977 | Haker | 249/54 |
| 4,116,416 | 9/1978 | Segura | 249/54 |
| 4,283,173 | 8/1981 | Browne et al. | 249/54 |
| 4,439,151 | 3/1984 | Whelan | 433/74 |
| 4,494,934 | 1/1985 | Huffman | 249/54 |
| 4,538,987 | 9/1985 | Weissman | 249/54 |
| 4,608,016 | 8/1986 | Zeiser | 433/74 |
| 4,708,648 | 11/1987 | Weissman | 433/74 |
| 4,708,835 | 11/1987 | Kiefer | 264/17 |
| 4,767,330 | 8/1988 | Burger | 433/213 |

FOREIGN PATENT DOCUMENTS

| | | | |
|---|---|---|---|
| 0210484 | 2/1987 | European Pat. Off. | 433/214 |
| 3505680 | 7/1985 | Fed. Rep. of Germany | . |
| 3521137 | 12/1986 | Fed. Rep. of Germany | . |

Primary Examiner—James C. Housel

[57] ABSTRACT

A base for holding a plaster of paris model for a set of teeth for the production of dentures, including a planar bottom to which is attached an upright circumferential exterior wall in the shape of a jaw. The base further includes perpendicularly projecting guide elements extending up from the bottom surface. The guide elements are tapered in the direction away from the bottom surface for example in the shape of a frustropyramid or frustocone and form at least one curved row which follows the curvature of the exterior wall in a U-shaped configuration. In preparing the plaster model within the base, the guide elements form corresponding holes in the plaster. The device may have a second U-shaped row of guide pins extending from the bottom surface to further guide and align the plaster mold when inserted into the base portion. This base then allows for the removal and reinsertion of a plaster of paris mold while maintaining the original and critical alignment of the model and or the individual pieces thereof.

12 Claims, 3 Drawing Sheets

BASE FOR HOLDING A PLASTER OF PARIS MODEL OF A SET OF TEETH

BACKGROUND OF THE INVENTION

The invention relates to a base for holding the plaster of paris model of a set of teeth in the preparation of dentures, the base including a bottom to which is attached an upright, circumferential exterior wall adapted to the shape of the jaw, with guide elements, for the plaster of paris model that can be sawed apart, projecting perpendicularly from the bottom.

The provided base is used in the production of dentures of any type, such as crowns, inserts, bridges and dental prostheses made of plastic, ceramics and metals.

Various embodiments of bases for holding the plaster of paris set of a patient's teeth made from a silicone rubber impression are already known. In the production of extensive dental prostheses, a model must be made of the teeth of the maxilla and of the mandible so that the proper interaction of the prosthesis with the existing teeth can be ensured. For this purpose, plaster of paris models of both jaws are inserted into an articulator—which simulates jaw movement—to thus constantly check the height and configuration of the chewing surfaces in the dental laboratory.

A horseshoe-shaped bar is known for fastening a plaster of paris model to a base provided with a bottom and an exterior wall, with such bar being disposed as a guide element on the base. However, this bar permits neither easy removal of the plaster of paris model or its parts from the base nor does it permit the precise, unmistakable repositioning of the removed parts (DE-OS 3,505,680). The use of a zigzag bar on the bottom also does not ensure accurate, unambiguous repositioning of the plaster of paris parts (DE-OS 3,521,137).

Also known is a base plate which includes a plurality of bores into which cylindrical or out-of-round guide elements can be pressed entirely as required. However, the manufacture of such a base is rather expensive, it can be employed only together with a correspondingly configured direction-finding plate and its manipulation is rather complicated. Since the guide elements are configured and provided to remain in the plaster of paris model or its parts, problems arise if a ceramic casting mass is employed which must be fired in a kiln. (DE-OS 3,436,094).

SUMMARY OF THE INVENTION

The object of the invention resides in the design of a base for releasably holding a plaster of paris model of a set of teeth or plaster parts severed therefrom, which permits accurate and unmistakable positioning of the removed parts, which is particularly easily manipulated and the use of which does not require any holding elements to remain either in the plaster of paris of the model or in parts of the model.

To solve the problem at hand, the invention is based on a known base which includes a bottom having an attached upright, circumferential exterior wall which is adapted to the shape of the jaw, with perpendicularly projecting guide elements for the plaster of paris model, which can be sawed apart, being disposed on the bottom. The problem is solved by at least U-shaped curved row of juxtaposed, spaced frustoconical or frustopyramidal pins as guide elements which are parallel to the interior face of the exterior wall. These frustum pins permit easy impression of the base into the still liquid plaster of paris for the model and also easy removal of the plaster of paris model. The arrangement of the pins in a Ushaped row prevents erroneous repositioning of parts of the model during manufacture of the denture. It is here of particular advantage that no foreign material elements remain in the plaster of paris model which could interfere during subsequent processing phases.

The casting box matching the base permits the easy manufacture of a second plaster of paris cast or of a ceramic model.

BRIEF DESCRIPTION OF THE DRAWINGS

The invention will be described in greater detail below with reference to an embodiment and the attached drawing sheets.

DETAILED DESCRIPTION OF AN EXEMPLARY EMBODIMENT

Figure 1:
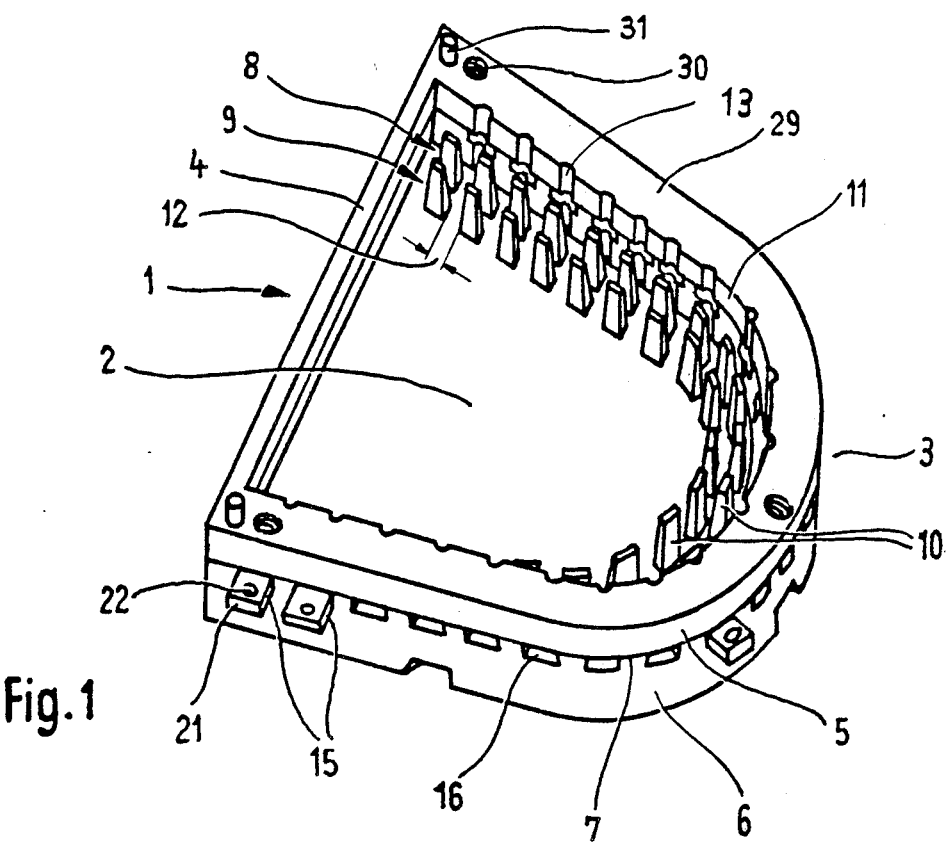
FIG. 1A, is a top perspective view of a base for holding a plaster of paris model of a set of teeth.
FIG. 1B is a partial view illustrating conical pins
Figure 2:
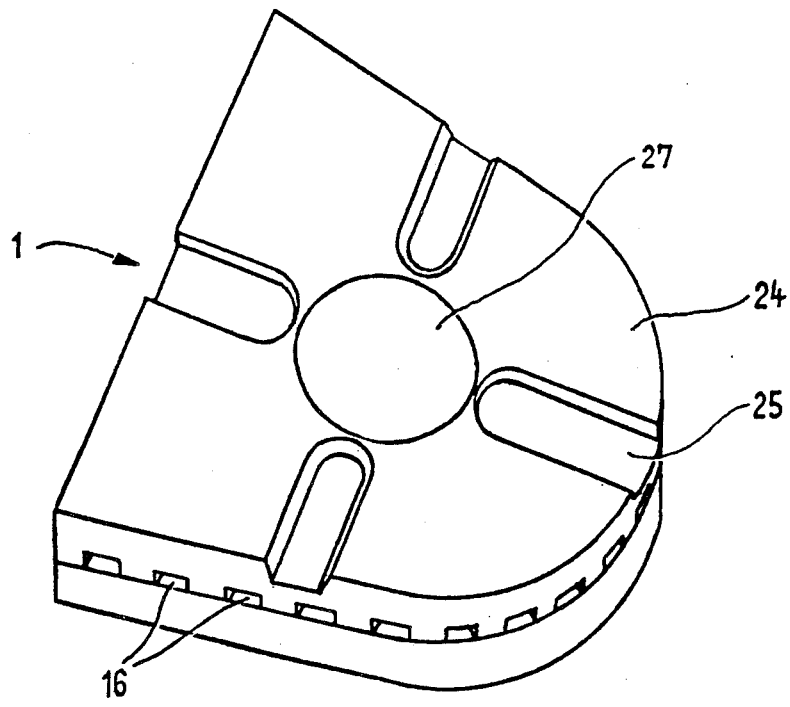
FIG. 2, is a perspective view of the underside of the base according to FIG. 1.

The base 1 shown in FIGS. 1 and 2 serves to hold the plaster of paris model of a set of teeth during the production of dentures of any type. This base 1 is composed of metal, for example of aluminum. It has a planar bottom 2 and a circumferential exterior wall 3. This exterior wall 3 has a U-shaped cross section and is adapted to the shape of the jaw; a straight rear wall 4 terminates the arcuate portion of exterior wall 3.

Exterior wall 3 is made of two parts and accordingly includes an upper member 5 as well as a lower member 6 shaped to bottom 2, with the interface 7 between upper member 5 and lower member 6 being planar and extending parallel to bottom 2. Upper member 5 is releasably fastened to lower member 6 by means of screws (not shown) and can therefore be removed if necessary.

At the bottom 2 of base 1, two U-shaped curved rows 8 and 9 of frustum configured pins 10 as illustrated in FIGS. 1A and B, are provided as guide elements for the removable plaster of paris model or its sawed-off parts. The first one of these rows 8 is parallel to the interior face 11 of exterior wall 3 and the second row 9 is parallel to the first row 8.

The pins 10 of the two rows 8 and 9 are offset with respect to one another and placed in respective gaps. The open spacing 12 between pins 10 varies; in the region of the greatest curvature of rows 8 and 9 it is about five millimeters while it is roughly seven millimeters toward the ends of the rows.

Alternatively, the spacing 12 between pins 10 may be substantially constant.

On its interior face 11, the exterior wall 3 of base 1 is equipped with mutually parallel guide grooves 13 having an approximately semicircular cross section and extending perpendicularly to bottom 2. The interior face 11 of exterior wall 3—see FIG. 5—stands at an angle 14 of somewhat more than ninety degrees to bottom 2.

Along its U-shaped curved portion, exterior wall 3 is provided with a plurality of locking bars 15 which are arranged to be displaceable in the direction toward pins 10 and parallel to bottom 2. These locking bars 15 have the shape of flat blocks and are displaceable in corresponding, likewise block-shaped recesses 16 in exterior wall 3. The interface 7 between upper member 5 and lower member 6 of exterior wall 3 extends through these recesses 16.

Figure 5:
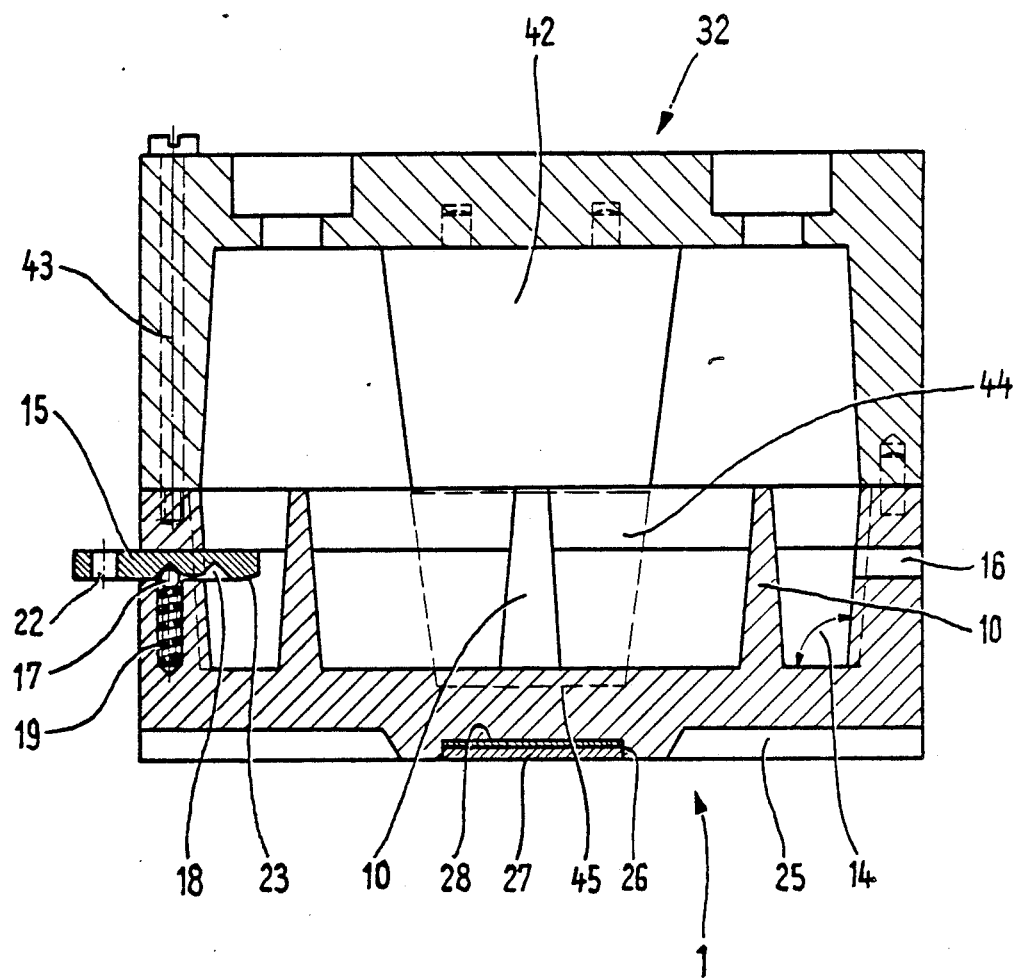
FIG. 5 is a cross-sectional view of the base according to FIGS. 1 and 2 with a casting box according to FIGS. 3 and 4 in place.

Detent elements 17 in the form of steel balls disposed in exterior wall 3 engage every locking bar 15 (see FIG. 5). On its side oriented toward bottom 2, each locking bar 15 is provided with two juxtaposed recesses 18 which are connected with one another by way of a small trough and into which engages the locking element 17 (the ball) which is under the influence of a pre-tensioned spring 19 disposed in a blind bore 20 of lower member 6 of exterior wall 3.

At their free outer ends 21, locking bars 15 are provided with circular openings 23 and at their opposite ends facing pins 10, they are provided with a slope 23 oriented toward bottom 2.

Four fitting grooves 25 having a trapezoidal cross section are provided at the underside 24 of bottom 2 of base 1 (see FIG. 2). These fitting grooves 25 have a semicircular end and are arranged at central angles of 90° each. In a recess 26 (see FIG. 5) of bottom 2, a circular plate 27 of a ferromagnetic material is inserted and fastened there by means of an adhesive 28.

Three threaded holes 30 are provided in the crown 29 of exterior wall 3 and two fitting pins 31 project there as well.

Figure 3:
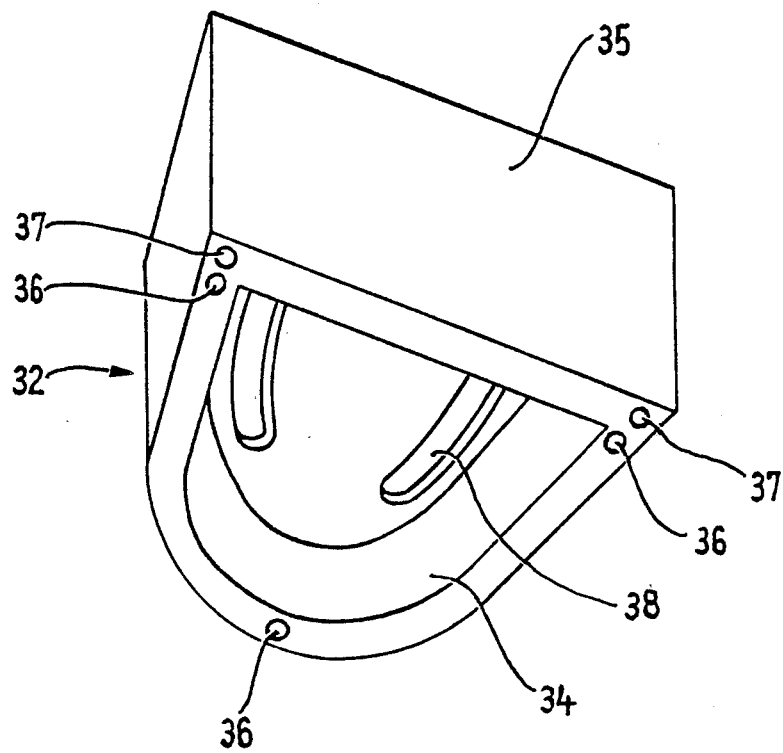
FIG. 3, is a likewise perspective view, seen from the bottom, of a casting box for the base.
Figure 4:
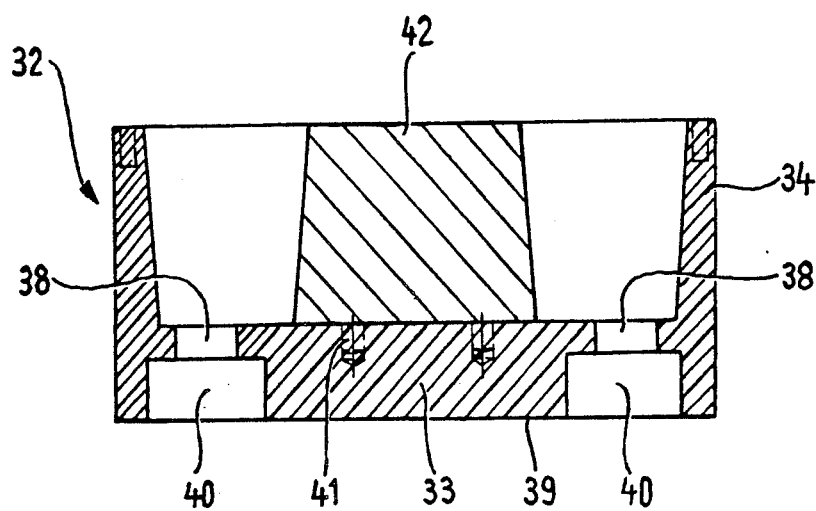
FIG. 4, is a cross-sectional view of the casting box according to FIG. 3 with a core inserted.

A casting box 32 (see FIGS. 3 and 4) can be placed onto base 1. This casting box 32 has a shape corresponding to base 1 and a shaped-on cover 33, a side wall 34 having a U-shaped cross section and a linear terminating wall 35. The side wall 34 of casting box 32 can be placed (as shown in FIG. 5) onto crown 29 of exterior wall 3 of base 1.

The side wall 34 of casting box 32 has three passage holes 36 which are flush with threaded holes 30 in exterior wall 3 of base 1. Side wall 34 also has two fitting bores 37 into which engage mating pins 31 when the casting box 32 is placed onto base 1.

Two fill openings 38 for a pourable casting mass are provided in cover 33 of casting box 32; at the exterior wall 39 of cover 33 these fill openings have widened sections 40.

A core 42 equipped with plug-in pins 41 is disposed in casting box 32.

With the aid of head screws 43 (indicated in FIG. 5) which pass through passage holes 36 and are screwed into threaded bores 30, casting box 32 can be fastened to base 1.

Manipulation of the proposed base 1 is conceivably simple. Once plater of paris for the model has been filled into a silicone rubber impression of the patient's teeth prepared by the dentist, base 1 and its pins 10 are pressed into the still liquid plaster of paris and locking bars 15 are pushed forward. After the plaster has hardened and the impression has been removed, the plaster of paris model is seated on base 1 and can easily be removed from it by pulling back locking bars 15 since the conical shape of pins 10 and of exterior wall 3 does not permit the plaster of paris to stick. The loosened plater of paris model can now be sawed apart and the resulting parts can be replaced again as often as desired, with it being impossible to inadvertently put any of the parts in the wrong position due to the position of the two rows 8 and 9 relative to one another and the different spacings between pins 10.

To produce a further dental model of plaster of paris or a model of a refractory ceramic mass, a casting box 32 is placed onto the base 1 carrying the plaster of paris model and is fastened there with the aid of head screws 43. Now a molding mass can be filled in through fill openings 38 and is anchored in widened sections 40. Once the molding mass has set and the denture model has been removed together with base 1, the resulting negative can be cast in plaster of paris or a ceramic mass into which a second base and its pins are pressed.

To temporarily fasten the base 1 carrying the plaster of paris model in an articulator (not shown), fitting grooves are provided which ensure precise lateral alignment in conjunction with a ferromagnetic plate 27 which is disposed opposite a permanent magnet in the articulator.

A conical, insertable core member 44 (indicated by dashes in FIG. 5) may be disposed at the bottom 2 of base 1; it is removed if the palate is to remain exposed. This core member 44 is seated in a recess 45 in bottom 2.

I claim:

1. Base for holding a plaster of paris model of a set of teeth for the production of dentures, the base including a bottom having a first surface to which is attached an upright, circumferential U-shaped exterior wall having an interior surface and perpendicularly projecting guide elements for the plaster of paris model, wherein said guide elements include a first U-shaped curved row of spaced, juxtaposed, frustum configured pins extending parallel to the interior surface of said exterior wall.

2. Base according to claim 1, further including a second U-shaped curved row of pins adjacent said first row.

3. Base according to claim 1, wherein each of the pins of said first row are substantially equally spaced along said row.

4. Base according to claim 1, wherein, the exterior wall is provided with parallel guide grooves on said interior surface which are perpendicular to the bottom.

5. Base according to claim 1, wherein the interior surface of the exterior wall forms an angle of somewhat greater than ninety degrees with respect to the bottom.

6. Base according to claim 1, wherein fitting grooves are provided on a second surface of the bottom opposite said first surface.

7. Base according to claim 1, wherein a plate of ferromagnetic material is disposed on a second surface of the bottom opposite said first surface.

8. Base according to claim 1, further including fitting means for alignment with a casting box provided crown on the exterior wall.

9. Base according to claim 1, wherein said frustum configured pins are frustopyramidal in shape.

10. Base according to claim 1, wherein said frustum configured pins are frustoconical in shape.

11. Casting apparatus for the production of dentures, comprising:
a base for holding a plaster of paris model of a set of teeth for the production of said dentures, the base including a bottom to which is attached an upright, circumferential U-shaped exterior wall having an interior surface and perpendicularly projecting guide elements for the plaster of paris model, wherein said guide elements include a first U- shaped curved row of spaced, juxtaposed, frustum configured pins extending parallel to the interior surface of said exterior wall, and a casting box having a cover and a side wall depending from said cover, said side wall being configured for abutting said exterior wall.

12. Apparatus according to claim 11, further comprising:

first fitting means on said exterior wall of said base, and second fitting means on said side wall of the casting box is provided with fitting means which correspond with said first fitting means for alignment of said base and said box of the base.

* * * * *